United States Patent [19]

Lawson et al.

[11] 4,021,562

[45] May 3, 1977

[54] 4-TERTIARY-AMINO-2,6-DIAMINOPYRIDINE 1-OXIDES

[75] Inventors: John E. Lawson; Ronald D. Dennis, both of Evansville, Ind.

[73] Assignee: Mead Johnson & Company, Evansville, Ind.

[22] Filed: Dec. 8, 1975

[21] Appl. No.: 638,473

[52] U.S. Cl. .......................... 424/267; 260/243 B; 260/247.5 G; 260/268 H; 260/296 R; 260/293.69; 260/296 H; 424/246; 424/248.56; 424/250; 424/263; 260/247.2 B; 260/295 AM

[51] Int. Cl.² ............. C07D 213/74; C07D 401/04; C07D 413/04; C07D 417/04

[58] Field of Search .................. 260/293.69, 296 R; 424/263, 267

[56] References Cited

UNITED STATES PATENTS

| 3,329,569 | 7/1967 | Tedeschi et al. | 260/296 R |
| 3,382,248 | 5/1968 | Anthony et al. | 260/256.4 |

FOREIGN PATENTS OR APPLICATIONS 1,355,461  6/1974  United Kingdom ........... 260/296 R

*Primary Examiner*—Henry R. Jiles
*Assistant Examiner*—Robert T. Bond
*Attorney, Agent, or Firm*—R. H. Uloth; R. E. Carnahan

[57] ABSTRACT

A series of 2,6-diamino-4-tertiary-amino-pyridine 1-oxides is disclosed. Substituents in the 4-position include diethylamino, pyrrolidinyl, piperidino, morpholino, thiomorpholino, and N-methylpiperazino. Novel oxadiazolones such as 5-amino-7-(1-piperidinyl)-2H-[1,2,4]-oxadiazolo[2,3-a]pyridine-2-one which are useful in the preparation of the pyridine 1-oxides are also disclosed. The compounds of this invention lower blood pressure in normotensive and hypertensive mammals and are particularly useful in the treatment of hypertensive conditions in mammals. 2,6-Diamino-4-(1-piperidinyl)pyridine 1-oxide is a representative embodiment of the invention.

9 Claims, No Drawings

4-TERTIARY-AMINO-2,6-DIAMINOPYRIDINE 1-OXIDES

BACKGROUND OF THE INVENTION

The present invention is concerned with 4-tertiary-amino-2,6-diaminopyridine 1-oxides and pharmaceutically acceptable acid addition salts thereof. It is further concerned with a process for making the foregoing compounds, intermediates useful in the preparation thereof and to an antihypertensive therapeutic process.

References illustrating the state of the art relating to the compounds of the instant invention are British Patent 1,355,461 and U.S. Pat. Nos. 3,329,569 and 3,382,248.

British patent 1,355,461 discloses 4-amino-2-loweralkyl-6-substituted-pyridine 1-oxides such as 6-amino-4-piperidino-2-picoline-1-oxide and teaches that the compounds are active as hypotensive agents.

U.S. Pat. No. 3,329,569 relates to a series of 2,6-diamino-4-substituted-pyridines and corresponding N-oxides wherein substitution in the 4-position includes alkoxy and phenoxy. The patent teaches that administration of the compounds to normotensive and hypertensive dogs results in a significant drop in blood pressure.

U.S. Pat. No. 3,382,248 relates to 6-amino-1,2-dihydro-1-hydroxy-2-iminopyrimidines such as 6-amino-1,2-dihydro-1-hydroxy-2-imino-4-piperidinopyrimidine. The compounds are reported to be useful as antihypertensive agents, antifertility agents, anti-inflammatory agents and as central nervous system stimulants.

SUMMARY OF THE INVENTION

This invention pertains to novel 4-tertiary-amino-2,6-diaminopyridine 1-oxides and pharmaceutically acceptable acid addition salts thereof characterized by Formula I

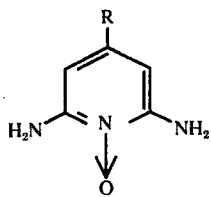

Formula I wherein R is selected from the group of radicals consisting of diethylamino, pyrrolidino, piperidino, morpholino, thiomorpholino, and N-methylpiperazino.

The term "pharmaceutically acceptable acid addition salt" used herein denotes a salt form of a 4-tertiary-amino-2,6-diaminopyridine 1-oxide base of Formula I obtained by combination with inorganic or organic acids. Suitable acids which may be used to form pharmacologically acceptable acid addition salts are those acids which are relatively nontoxic in their anionic form such as sulfuric, hydrochloric, phosphoric, hydrobomic, hydroiodic, sulfamic, methanesulfonic, benzenesulfonic, p-toluenesulfonic, acetic, lactic, succinic, maleic, mucic, tartaric, citric, gluconic, benzoic, cinnamic, isethionic, fumaric, and related acids. Preparation of acid addition salts is accomplished in conventional fashion by treating the base for Formula I in a suitable organic solvent such as ethanol, benzene, ether, chloroform, etc., with at least one molecular equivalent of the acid. Isolation of the salt is carried out by conventional techniques. For instance, the acidified solution is concentrated or the product precipitated by the addition of a co-solvent such as ether, isopropyl ether, ethyl acetate and the like in which the salt has limited solubility. Both mono- and diacid-addition salts are considered within the purview of the invention.

The 4-tertiary-amino-2,6-diaminopyridine 1-oxides of Formula I are obtained by reacting a compound of Formula II

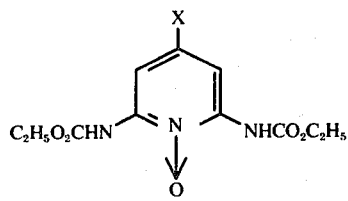

Formula II wherein X is halogen with a R-H secondary amine wherein R is as defined above. Displacement of the halogen atom (preferably chlorine or bromine) by the R-H amine is accompanied by aminolysis of the ethoxycarbonylamino groups in the 2,6-position at the "C-N" bond to provide the compounds of Formula I. In addition to Formula I compounds, mono- and bis-ureides corresponding to Formula III and IV, respectively, wherein R is as defined above are obtained as a result of interaction of the R-H amine with the 2,6-ethoxycarbonylamino groups. The compounds of Formulas III and IV are useful as intermediates in the preparation of the compounds of Formula I

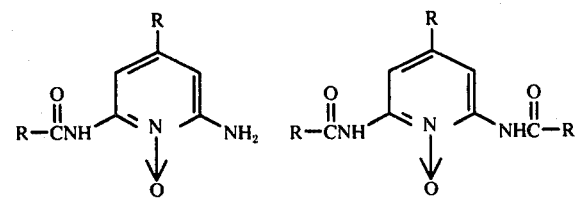

Formula III      Formula IV

If desired, the product of Formula I can be isolated from the reaction mixture containing the compounds of Formula III and IV by conventional methods such as crystallization of the concentrated reaction mixture or chromatographic separation thereof. However, the preferred procedure is to convert the Formula III and IV compounds obtained following displacement of the halogen to the desired Formula I product by hydrolyzing the concentrated reaction mixture with an alkali base such as potassium hydroxide.

The displacement of the halogen atom of the starting material of Formula II with the secondary R-H amine is carried out in the temperature range of 100°–200° C. and preferably in the range of 125°–175° C. In view of competing reactions mentioned above which result in compounds of Formula III and IV along with the desired compounds of Formula I at least three molecular equivalents of the R-H amine to the Formula II chloro compound is employed. Preferably, sufficient R-H amine is used in order that a homogenous mixture is obtained when the reactants are mixed and heated.

Treating the mono-ureides of Formula III with dilute acid results in hydrolysis of the ureide and cyclization to provide novel oxadiazolones of Formula V wherein R is as defined above.

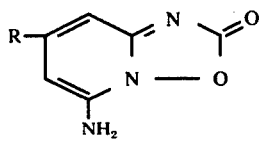

Formula V

Compounds of Formula V are readily converted to compounds of Formula I by alkaline hydrolysis and accordingly are valuable intermediates.

Illustrative of compounds of the invention prepared according to the foregoing methods are:
2,6-diamino-4-(1-piperidinyl)pyridine 1-oxide,
2,6-diamino-4-(4-morpholinyl)pyridine 1-oxide,
2,6-diamino-4-(pyrrolidino)pyridine 1-oxide,
2,6-diamino-4-(diethylamino)pyridine 1-oxide,
2,6-diamino-4-(thiomorpholino)pyridine 1-oxide,
2,6-diamino-4-(N-methylpiperazino)pyridine 1-oxide, which are obtained by reaction of 4-chloro-2,6-bis-(ethoxycarbonylamino)-pyridine 1-oxide with the respective amines: piperidine, morpholine, pyrrolidine, diethylamine, thiomorpholine and N-methylpiperazine, respectively.

The 4-tertiary-amino-2,6-diaminopyridine 1-oxides of Formula I, pharmaceutically acid addition salts thereof, and the compounds of Formula V have hypotensive and antihypertensive properties and are, therefore, useful in treating conditions in mammals responsive to administration of such agents. They are orally and parenterally active. Standard pharmacological tests can be employed to demonstrate the hypotensive and antihypertensive utility of the instant compounds. For example, intravenous administration of 2,6-diamino-4-(1-piperidinyl)pyridine 1-oxide to the anesthetized normotensive dog in a dosage range of from 0.1 to 10 mg./kg. body weight provides a dose related reduction in blood pressure. In the spontaneous hypertensive rat, oral administration of 2,6-diamino-4-(1-piperidinyl)pyridine 1-oxide at a dose of 2.5 mg./kg. body weight provides a reduction in blood pressure of 50 mm. Hg. The desirable antihypertensive effects are obtained with no adverse toxicity.

A feature of the instant invention includes a method of reducing blood pressure in a mammal in need thereof comprising systemic administration to the mammal a substantially nontoxic, effective dose to reduce blood pressure of from 0.1 to 10 mg./kg. body weight of a compound of Formula I or a pharmaceutically acceptable salt thereof or a compound of Formula V. The term systemic administration as used herein includes both oral and parenteral routes such as intramuscular, intraveneous, intraperitoneal and subcutaneous. The dosage will vary to some extent with the form of administration and the particular compound chosen. Generally, the compound is administered at a dosage substantially less than the dose of the compound which is thought to be effective. Thereafter, in conformity with accepted therapeutic methods, the dosage is increased by small increments until the desired antihypertensive or hypotensive effect is reached.

The 4-substituted-2,6-diaminopyridine 1-oxides of Formula I and pharmaceutically acceptable salts thereof can be formulated according to conventional pharmaceutical practice to provide pharmaceutical compositions of unit dosage form. Such compositions include solid or liquid dosage forms such as tablets, capsules, powders, pills, granules, emulsions, suspensions, syrups, elixirs, suppositories, sterile aqueous or vegetable oil dispersion and the like. For most purposes, unit dosage forms containing from 5 to 500 mg. of one of the compounds of Formula I with a pharmaceutically acceptable carrier are suitable.

Powders are prepared by comminuting the active ingredient to a suitable fine size and mixing and a similarly comminuted diluent. The diluent can be edible carbohydrate material such as starch. Sweetening and flavoring agents can be combined with the powders as desired.

The tablets are made from a powder mixture, by granulating or slugging, adding a lubricant and pressing into tablets. The powder mixture is prepared by mixing the active ingredient in a suitable comminuted form with a diluent or base such as starch, lactose, dicalcium phosphate, calcium sulfate, and the like. The powder mixture can be granulated by wetting with a binder such as syrup, gelatin solution, methylcellulose solution or acacia mucilage and forcing through a screen. As an alternative to wet granulation, the powder mixture can be slugged (i.e., run through a tablet machine) and the resulting large tablets broken down into granules. The granules are further lubricated to prevent sticking in the tablet forming dyes by means of addition of stearic acid, a stearate salt, talc, or mineral oil. The lubricated mixture is then compressed into tablets. If desired, the tablet can be provided with a protective coating consisting of a sealing coat of shellac, a coating of sugar and methyl cellulose, and a polish coating of carnuba wax.

Capsules are produced by preparing a powder mixture as hereinabove described and filling into formed gelatin capsules. Lubricants, such as talc, magnesium stearate and calcium stearate, may be added to the powder mixture before the filling operation.

For oral administration, unit dosage form such as syrups and elixirs wherein each teaspoon full of composition contains a predetermined amount of active ingredient are useful. A syrup is prepared by dispersing the active ingredient in a suitably flavored aqueous sucrose solution. Similarly, an elixir is prepared utilizing an aqueous-alcoholic vehicle.

In preparing parenteral unit dosage forms for administration, a measured amount of active ingredient is placed in a vial and the vial and its contents are sterilized and sealed.

The compounds which constitute this invention and their methods of preparation will appear more fully from a consideration of the following examples and apended claims which are given for the purpose of illustration only and are not to be construed as limiting the invention in sphere or in scope.

With reference to the "NMR" data given below, tetramethylsilane was employed as the internal reference peak and chemical shift delta values are in parts per million. The following multiplicity notations are employed: $s$ = singlet, $d$ = doublet, $t$ = triplet, $m$ = multiplet (center listed), $q$ = quintuplet, $bs$ = broad singlet.

EXAMPLE 1

2,6-Diamino-4-(4-morpholinyl)pyridine 1-oxide Hydrochloride Hydrate a. A mixture of 4-chloro-2,6-bis(ethoxycarbonylamino)-pyridine (148.0 g., 0.51 mole), 296 ml. of acetic acid, and 250 ml. of 40% peracetic acid is stirred at 70° C. for 3 hr. The hot solution is poured into 4 liters of ice water providing a solid which is collected, washed with water and air dried. Crystallization of the dried solid from 3 liters of 95% ethanol affords 118.0 g. (76% yield), of 4-chloro-2,6-bis(ethoxycarbonylamino)pyridine 1-oxide having a melting point of 146°–149° C. Recrystallization of this material from 95% ethanol affords analytically pure 4-chloro-2,6-bis-(ethoxycarbonylamino)pyridine 1-oxide, m.p. 149.5°–150.5° C.

Analysis. Calcd. for $C_{11}H_{14}ClN_3O_5$ (percent): C, 43.50; H, 4.65; N, 13.84; Cl, 11.67. Found (percent): C, 43.61; H, 4.55; N, 13.77; Cl, 11.76.

NMR (CDCl$_3$): 1.31 (t, 6H, 7.0 Hz); 4.28 (q, 4H, 7.0 Hz); 7.84 (s, 2H); 8.80 (bs, 2H).

b. A mixture of 4-chloro-2,6-bis(ethoxycarbonylamino)pyridine 1-oxide (10.0 g., 0.03 mole) and 60 ml. of morpholine is refluxed with stirring under a nitrogen atmosphere for a period of 24 hrs. and concentrated to dryness. The residual material thus obtained is taken up in 200 ml. of absolute ethanol and 24.0 g. (0.36 mole) of 85% potassium hydroxide. After stirring at reflux temperature for a period of 16 hr., 200 ml. of absolute ethanol is added and reflux continued for an additional period of 30 hr. Concentration of the basic solution to dryness provides a residue which on stirring with water affords 4.4 g. (69% yield) of 2,6-diamino-4-(4-morpholinyl)-pyridine 1-oxide as the free base, m.p. 315°–325° C. (dec.). The free base is taken up in absolute ethanol and acidified with ethanolic hydrogen chloride. Addition of ethyl acetate to the acidified ethanolic solution and cooling affords the product which is collected and crystallized from absolute ethanol to provide 2.8 g. of analytically pure 2,6-diamino-4-(4-morpholinyl)pyridine 1-oxide hydrochloride hydrate, m.p. 203.5°–206.5° C. (dec.) (corr.).

Analysis. Calcd. for $C_9H_{14}N_4O_2 \cdot HCl \cdot H_2O$ (percent): C, 40.84; H, 6.47; N, 21.16. Found (percent): C, 41.10; H, 6.67; N, 21.40.

NMR (DMSO-d$_6$): 3.23 (m, 4H); 3.68 (m, 4H); 5.67 (s, 2H); 7.22 (bs, 4H).

EXAMPLE 2

2,6-Diamino-4-(1-piperidinyl)pyridine 1-oxide a. A mixture of 4-chloro-2,6-bis-(ethoxycarbonylamino)-pyridine 1-oxide (10.0 g., 0.03 mole) obtained according to the procedure of Example 1(a) and 60 ml. of piperidine is heated in a sealed tube at 135° C. for a period of 48 hr. The reaction mixture is concentrated to dryness and the residual material taken up in a mixture of chloroform and 10% aqueous sodium carbonate. After separating the organic and aqueous fractions, the aqueous layer is washed with chloroform, the chloroform fractions combined and dried over magnesium sulfate. The dried chloroform extract is concentrated to a volume of approximately 100 ml., cooled and filtered to afford 0.52 g., (8% yield) of 2,6-diamino-4-(1-piperidinyl)pyridine 1-oxide, m.p. 240°–265° C. (dec.).

b. The chloroform filtrate from Example 2(a) is concentrated and chromatographed on an alumina column employing chloroform as the eluant. Concentration of the chloroform effluant affords a residual material which crystallized from isopropyl ether provides 2.2 g. (17% yield) of 4-(1-piperidinyl)-2,6-bis[(1-piperidinylcarbonyl)amino]-pyridine 1-oxide, m.p. 125°–137° C. Further crystallization of this material from ethyl acetate affords analytically pure 4-(1-piperidinyl)-2,6-bis[(1-piperidinylcarbonyl)amino]pyridine 1-oxide, m.p. 136° C. to a cloudy melt clearing at 159.5° C.

Analysis. Calcd. for $C_{22}H_{34}N_6O_3$ (percent): C, 61.37; H, 7.96; N, 19.52. Found (percent): C, 61.05; H, 8.01; N, 19.44.

NMR (CDCl$_3$): 1.64 (m, 18H); 3.53 (m, 12H); 7.50 (s, 2H); 9.66 (bs, 2H).

c. The chloroform-eluted chromatographic column of Example 2(b) is further eluted with a solvent combination comprised of 9:1 chloroform-methanol. Concentration of the chloroform-methanol effluent provides 6.5 g. of solid material which crystallized from 95% ethanol and ethyl acetate affords analytically pure 2-amino-4-(1-piperidinyl)-6-[(1-piperidinylcarbonyl)amino]pyridine 1-oxide, m.p. 248.5°–249.5°C. (dec.).

Analysis. Calcd. for $C_{16}H_{25}N_5O_2$ (percent): C, 60.17; H, 7.89; N, 21.92. Found (percent): C, 59.99; H, 7.90; N, 21.93.

NMR (CDCl$_3$): 1.63 (m, 12H); 3.26 (m, 4H); 3.54 (m, 4H); 5.56 (bs, 2H); 5.75 (d, 1H, 3.0 Hz); 7.32 (d, 1H, 3.0 Hz); 9.90 (bs, 1H).

d. 2-Amino-4-(1-piperidinyl)-6-[(1-piperidinylcarbonyl)-amino]pyridine 1-oxide (5.37 g., 0.017 mole) is dissolved in 100 ml. of 3N hydrochloric acid. After stirring the acid mixture for 0.5 hr. at room temperature, the mixture is cooled and neutralized with 50% sodium hydroxide affording a solid. The solid is collected, washed with water and air dried to provide 3.7 g. of crude oxadiazolone product, m.p. 283° C. (dec.). Further purification is carried out by dissolving the crude product in 300 ml. of methanol and treating the solution with activated charcoal. Concentration of the methanol solution to a volume of approximately 125 ml. and cooling affords 2.9 g. (73% yield) of 5-amino-7-(1-piperidinyl)-2H-[1,2,4]oxadiazolo[2,3-a]-pyridin-2-one, m.p. 246.5° C. (dec.) (corr.).

Analysis. Calcd. for $C_{11}H_{14}N_4O_2$ (percent): C, 56.40; H, 6.02; N, 23.92. Found (percent): C, 56.52; H, 6.14; N, 23.92.

NMR (DMSO-d$_6$): 1.59 (m 6H); 3.37 (m, 4H); 5.61 (d, 1H, 3.0 Hz); 5.88 (d, 1H, 3.0 Hz); 7.15 (bs, 2H).

e. A mixture of 5-amino-7-(1-piperidinyl)-2H-[1,2,4]-oxadiazolo[2,3-a]pyridin-2-one (3.4 g., 0.014 mole) and 5.6 g. of potassium hydroxide in 85 ml. of absolute ethanol is refluxed for a period of 6 hr. and then concentrated under reduced vacuum to dryness. The residue thus obtained triturated with water affords 1.5 g. (51% yield) of product having a melting point of 280°–283° C. (dec.). Crystallization of this material from ethyl acetate-ethanol affords analytically pure 2,6-diamino-4-(1-piperidinyl)pyridine 1-oxide, m.p. 277° C. (dec.) (corr.).

Analysis. Calcd. for $C_{10}H_{16}N_4O$ (percent): C, 57.67; H, 7.74; N, 26.90. Found (percent): C, 57.53; H, 7.89; N, 26.70.

NMR (DMSO-d$_6$): 1.53 (m, 6H); 3.10 (m, 4H); 5.58 (s, 2H); 6.31 (bs, 4H).

f. The concentrated reaction mixture obtained from reaction of 4-chloro-2,6-bis-(ethoxycarbonylamino)- pyridine 1-oxide and piperidine in Example 2(a) hydrolyzed with potassium hydroxide in ethanol according to the procedure described in Example 1(b) provides 2,6-diamino-4-(1-piperidinyl)pyridine 1-oxide. Acidification of 2,6-diamino-4-(1-piperidinyl)pyridine 1-oxide in ethanol with ethanolic hydrogen chloride affords 2,6-diamino-4-(1-piperidinyl)pyridine 1-oxide hydrochloride.

Substituting piperidine for morpholine in the procedure of Example 1(b) affords 2,6-diamino-4-(1-piperidinyl)pyridine 1-oxide.

EXAMPLE 3

Pharmaceutical Compositions

The 2,6-diamino-4-tertiary-amino-pyridine 1-oxides characterized by Formula I are compounded with pharmacologically acceptable carriers to provide compositions useful in the present invention. Typical of the pharmaceutical compositions are the following:

a. Tablets

The 2,6-diamino-4-tertiary-amino-pyridine 1-oxides of Formula I are compounded into tablets according to the following example.

| Material | Amount |
|---|---|
| 2,6-diamino-4-(1-piperidinyl)pyridine 1-oxide | 50.0 g. |
| Magnesium stearate | 1.3 g. |
| Corn starch | 12.4 g. |
| Corn starch pregelatinized | 1.3 g. |
| Lactose | 185.0 g. |

The foregoing materials are blended in a twin-shell blender and then granulated and pressed into tablets weighing 200 mg. each. Each tablet contains 40 mg. of active ingredient. The tablet may be scored in quarters so that a dose of 10 mg. of active ingredient may be conveniently obtained.

b. Capsules

The 2,6-diamino-4-tertiary-amino-pyridine 1-oxides are compounded into capsules according to the proportions set forth in the following example.

| Material | Amount |
|---|---|
| Active ingredient | 25.0 mg. |
| Lactose | 246.0 mg. |
| Magnesium stearate | 4.0 mg. |

The foregoing materials are blended in a twin-shell blender and then filled into No. 1 hard gelatin capsules. Each capsule contains 25 mg. of active ingredient.

What is claimed is:

1. A compound having the formula

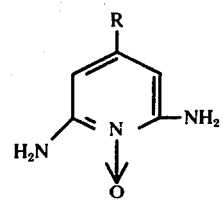

or a pharmaceutically acceptable acid addition salt thereof wherein R is selected from the group consisting of pyrrolidino, piperidino, and diethylamino.

2. The compound according to claim 1, which is 2,6-diamino-4-(1-piperidinyl)pyridine 1-oxide.

3. The compound of claim 1 which is 2,6-diamino-4-(1-piperidinyl)pyridine 1-oxide hydrochloride.

4. A method for reducing mammalian blood pressure comprising systemic administration to a mammal in need thereof of a substantially nontoxic effective dose to reduce the blood pressure of from about 0.1 to 10 mg./kg. body weight of a compound having the formula

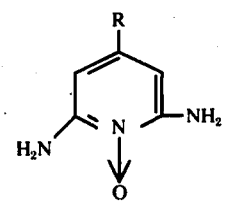

or a pharmaceutically acceptable acid addition salt thereof wherein R is selected from the group consisting of pyrrolidino, piperidino, and diethylamino.

5. The method as claimed in claim 4 wherein the compound employed is 2,5-diamino-4-(1-piperidinyl)-pyridine 1-oxide hydrochloride.

6. The method as claimed in claim 4 wherein the compound employed is 2,5-diamino-4-(1-piperidinyl)-pyridine 1-oxide.

7. A pharmaceutically acceptable composition for reducing mammalian blood pressure in dosage unit form for systemic administration to a mammal comprising a pharmaceutically acceptable carrier containing from 5 to 500 milligrams of an active ingredient selected from the group consisting of a compound having the formula

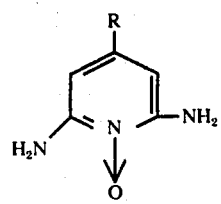

or a pharmaceutically acceptable acid addition salt thereof wherein R is selected from the group consisting of pyrrolidine, piperidino, and diethylamino.

8. The pharmaceutical composition according to claim 7 wherein the active ingredient is 2,6-diamino-4-(1-piperidinyl)pyridine 1-oxide.

9. The pharmaceutical composition according to claim 7 wherein the active ingredient is 2,6-diamino-4-(1-piperidinyl)pyridine 1-oxide hydrochloride.

* * * * *